United States Patent [19]
Jubin, Jr.

[11] Patent Number: 5,466,836
[45] Date of Patent: Nov. 14, 1995

[54] CATALYTIC CONVERTER AND METHOD FOR HIGHLY EXOTHERMIC REACTIONS

[75] Inventor: John C. Jubin, Jr., West Chester, Pa.

[73] Assignee: ARCO Chemical Technology, L.P., Greenville, Del.

[21] Appl. No.: 310,546

[22] Filed: Sep. 22, 1994

Related U.S. Application Data

[63] Continuation-in-part of Ser. No. 171,144, Dec. 20, 1993, abandoned.

[51] Int. Cl.$^6$ .................. C07D 301/12; C07D 303/04; B01J 8/04
[52] U.S. Cl. ................................ 549/531; 422/190
[58] Field of Search ................................ 549/531

[56] References Cited

U.S. PATENT DOCUMENTS

| | | |
|---|---|---|
| 2,271,646 | 2/1942 | Kassel . |
| 2,322,366 | 6/1943 | Kassel . |
| 2,579,580 | 12/1951 | Howk et al. ............................ 558/438 |
| 2,938,040 | 5/1960 | Skinner et al. ........................ 549/531 |
| 3,324,164 | 6/1967 | Merkel et al. ........................ 558/438 |
| 4,824,976 | 4/1989 | Clerici et al. ........................ 549/531 |
| 4,833,260 | 5/1989 | Neri et al. ............................ 549/531 |
| 5,214,168 | 5/1993 | Zajacek et al. . |

*Primary Examiner*—Joseph E. Evans
*Attorney, Agent, or Firm*—William C. Long

[57] ABSTRACT

A reactor is provided for carrying out highly exothermic reaction between liquids such as hydrogen peroxide and propylene. The reactor is made up of a series of separate zones containing a packed bed of solid catalyst; liquid from each zone is cooled with the main portion recycled to the same zone and a minor portion passing to the next successive zone.

6 Claims, 3 Drawing Sheets

CATALYTIC CONVERTER AND METHOD FOR HIGHLY EXOTHERMIC REACTIONS

RELATED APPLICATION

This application is a continuation-in-part of application Ser. No. 08/171,144 filed Dec. 20, 1993 now abandoned.

BACKGROUND OF THE INVENTION

1. Field of the Invention

The present invention relates to a catalytic converter or reactor and a process for carrying out highly exothermic reactions.

2. Description of the Prior Art

Substantial difficulties are encountered in carrying out highly exothermic reactions where reactants and/or products are temperature sensitive. For example, the catalytic liquid phase reaction of propylene and hydrogen peroxide to produce propylene oxide is a highly exothermic reaction while hydrogen peroxide decomposition is quite temperature sensitive. Thus, removal of the exothermic heat of reaction without causing excess temperature rise presents a serious problem.

Conventional reactors for exothermic reactions are usually of two types:

(1) Quench type which consist of multiple fixed beds with cold feed quench injected in between beds (2) Tubular type in which the catalyst is placed in the tubes of a vertical shell and tube heat exchanger If the heat of reaction is high, the first type does not provide sufficient heat removal. This can be overcome by recycling cold reactor effluent but this results in the disadvantages associated with back-mixed reactors.

The tubular reactor cost becomes prohibitive when high heats of reaction have to be removed through heat exchanger surfaces operating with a low heat transfer coefficient. There is also a temperature gradient from the center of the tube which is often detrimental to a process which requires nearly isothermal conditions.

U.S. Pat. Nos. 2,271,646 and 2,322,366 provide catalytic converters for use in catalytic cracking and the like reactions wherein the converters are divided into a series of zones and the reaction mixture from one zone is removed and externally heated or cooled before being returned to the next reaction zone. Such converters are not suitable for the effective temperature and reagent concentration control of a highly exothermic system as is achieved in accordance with the present invention.

BRIEF DESCRIPTION OF THE INVENTION

In accordance with the present invention, a catalytic converter tower is provided containing a series of separate zones each having a bed of solid catalyst contained therein. Liquid reaction mixture containing the appropriate reactants is introduced into a zone and passed at reaction conditions through the catalyst bed. The resulting reaction mixture is removed from the reactor and the exothermic heat of reaction is removed by indirect heat exchange. The great bulk of the cooled reaction mixture is recycled to the zone from which it was removed while a smaller portion is passed to the next zone and reacted in a similar fashion.

The recycle of the great bulk of the reaction mixture after cooling insures that only a modest temperature rise takes place in any one reaction zone. The provision of separate reaction zones enables close control of the reaction compositions approaching a plug flow reactor configuration.

DESCRIPTION OF THE DRAWING

The accompanying drawings.

DETAILED DESCRIPTION

Practice of the invention is especially applicable to highly exothermic reactions such as that between propylene and hydrogen peroxide to form propylene oxide. In such a reaction, heat of reaction must be removed and the reaction temperature must be carefully controlled in order to achieve optimum results.

Figure 1:
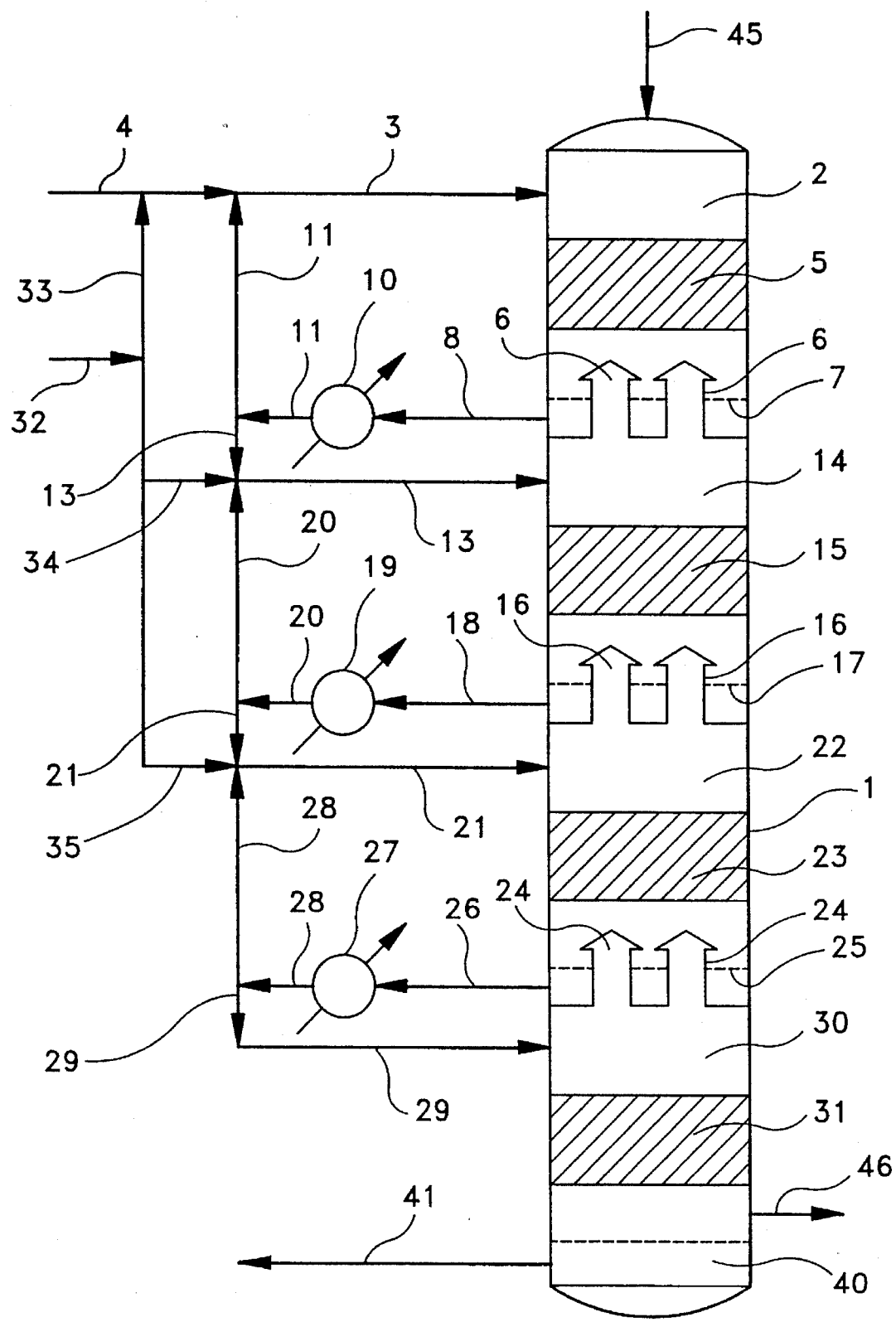
FIGS. 1–3, illustrate the improved reactor and various practices of the invention.

Referring to the attached drawing, FIG. 1, a four zone reactor 1 is illustrated. Each of the zones is provided with liquid inlet means near the upper part thereof, a packed bed of solid catalyst particles, liquid withdrawal means near the bottom of each zone, and vapor passage means permitting vapor to pass from one zone to the next; the lowest zone is not provided with the vapor passage means.

As shown in FIG. 1 and with reference to the production of propylene oxide by reaction of hydrogen peroxide and propylene, feed propylene and a hydrogen peroxide containing solution as well as recycled cooled reaction mixture containing unreacted propylene and hydrogen peroxide together with product propylene oxide is introduced into zone 2 via line 3. Net hydrogen peroxide feed is introduced into line 3 via line 4. Net propylene is introduced via lines 32 and 33 as liquid. The liquid mixture passes downwardly through packed catalyst bed 5 wherein the exothermic reaction of propylene and hydrogen peroxide to form propylene oxide takes place and there is a modest temperature increase of the mixture as a result of the reaction exotherm.

The reaction mixture passes through catalyst bed 5 into the lower section of zone 2. Risers 6 are provided permitting vapor passage downwardly to the next lower zone but preventing passage of liquid therethrough. Liquid level 7 is maintained in the lower section of zone 2 by known liquid level control means.

Liquid reaction mixture is withdrawn from zone 2 via line 8 and passes to indirect heat exchanger 10 wherein the reaction exotherm is removed and the circulating mixture is cooled to about its original temperature.

Most of the cooled mixture passes via lines 11 and 3 back to zone 2 together with the net propylene and hydrogen peroxide feed.

A minor portion of the cooled reaction mixture from zone 2 passes from cooler 10 via lines 11 and 13 to reaction zone 14 in combination with cooled recycle liquid from zone 14 and additional net liquid propylene added via lines 32 and 34.

Zone 14 is essentially similar to zone 2 with the reaction liquid passing downwardly through packed catalyst bed 15 wherein further reaction of hydrogen peroxide with propylene takes place. Risers 16 permit vapor passage therethrough and liquid level 17 is maintained in the lower section of zone 14.

Reaction liquid passes from zone 14 via line 18, to heat exchanger 19 where the reaction exotherm generated in zone 14 is removed. Most of the liquid cooled in exchanger 19 passes via lines 20 and 13 back to zone 14. A minor portion passes via lines 20 and 21 to the next reaction zone 22 together with recycled reaction mixture form zone 22 and additional net liquid propylene introduced via lines 32 and 35.

Zone 22 is similar to the preceding zones. The reaction mixture is passed downwardly through catalyst bed 23 wherein further exothermic reaction of propylene and hydrogen peroxide takes place. Risers 24 permit vapor passage therethrough and liquid level 25 is maintained in the lower section of zone 22.

Reaction liquid passes from zone 22 via line 26 to heat exchanger 27 where the reaction exotherm generated in zone 22 is removed. Most of the cooled liquid passes from exchanger via lines 28 and 21 back to zone 22. A minor portion passes via lines 28 and 29 to the next reaction zone 30.

Zone 30 is similar to the preceding zones but being the bottom zone has no risers for vapor passage. The reaction mixture passes downwardly through bed 31 of packed catalyst wherein the reaction between propylene and hydrogen peroxide is completed. Product liquid is removed via line 41. The lowest reaction zone is essentially a zone where the last generally small amount of hydrogen peroxide is reacted. Normally there is not sufficient reaction exotherm to warrant cooling and partial recycle of the liquid removed therefrom.

In the reactor illustrated in FIG. 1, zone 38 is the lowest and last reaction zone although it will be apparent that a greater or lesser number of zones can be utilized.

A small amount of propylene vapor is introduced into zone 2 via line 45 for purposes of purging any oxygen formed by hydrogen peroxide decomposition. Vapor passes through each zone through catalyst beds 5, 15, 23, and 31 via risers 6, 16, and 24 and is removed as a purge stream via line 46.

There are several advantages which are achieved through practice of the invention. By circulating large quantities of reaction liquid, temperature increase in any one zone can be kept quite small. Due to removal of the exothermic heat by cooling the liquid from each zone, close control of the reaction conditions can be achieved. By maintaining the plurality of separate zones, plug flow reactor conditions are approached and the benefits of reduced product concentrations in the earlier zones are achieved.

In general, of the liquid reaction mixture removed from each zone of the reactor, 60 to 90% is recycled after cooling with 10 to 40% moving forward to the next zone. Generally, flow in each zone is maintained at a level sufficient to limit the temperature rise in a zone to about 10° to 30° C., preferably 5° to 15° C.

A feature of the production of propylene oxide by the present invention is that the selectivity and yields of the desired propylene oxide product are improved by maintaining lower concentrations of hydrogen peroxide and product propylene oxide in the reaction mixture. This can be readily accomplished by dividing the net hydrogen peroxide feed among the several reaction zones rather than feeding all of the net hydrogen peroxide to the first zone or by adding substantial quantities of a diluent such as isopropanol, methanol or mixtures to the first reaction zone or by a combination of these procedures.

Figure 2:
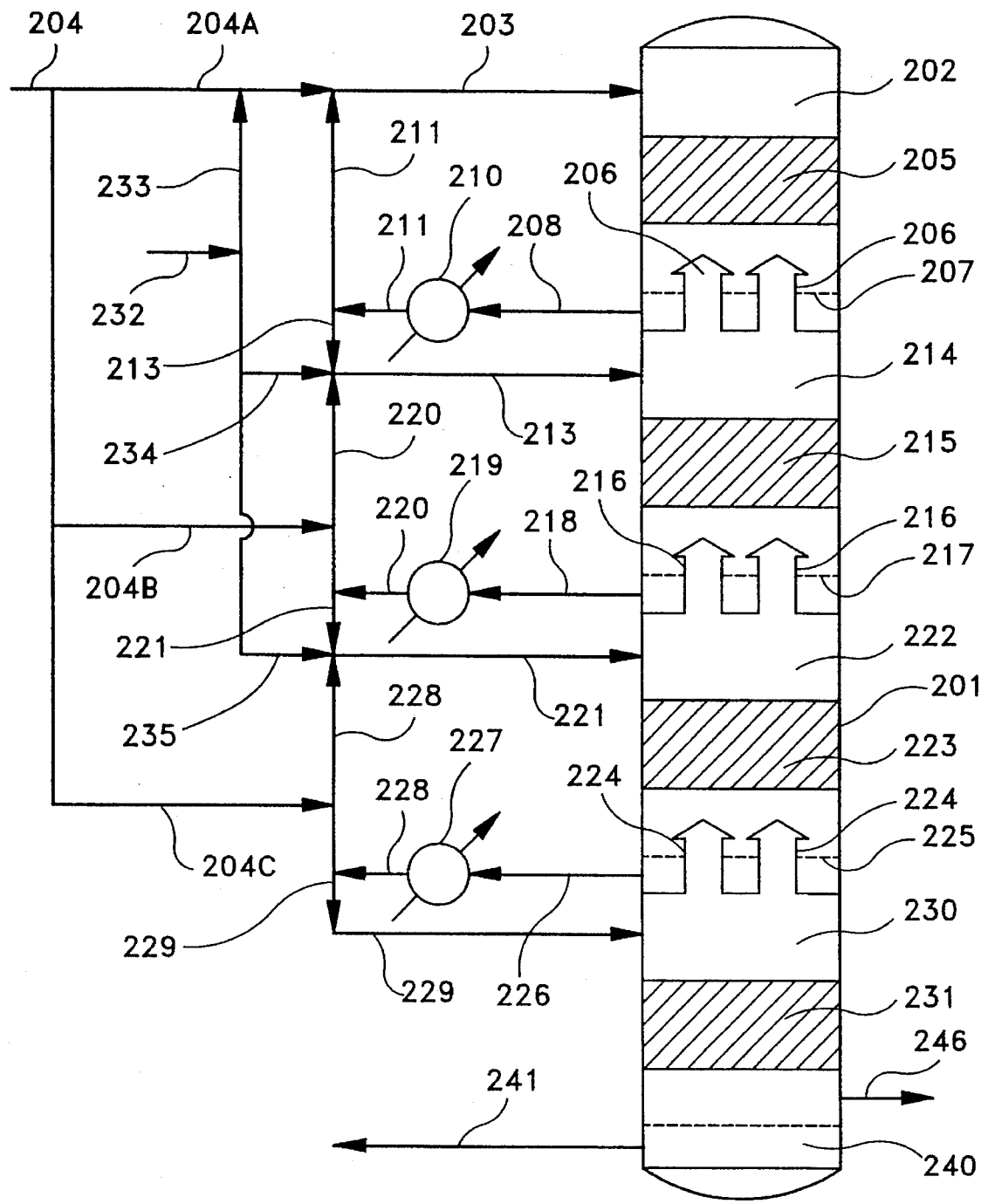

FIG. 2 illustrates a practice of the invention which is analogous to that shown in FIG. 1 except that the net hydrogen peroxide feed is divided and fed equally to the several reaction zones.

Figure 3:
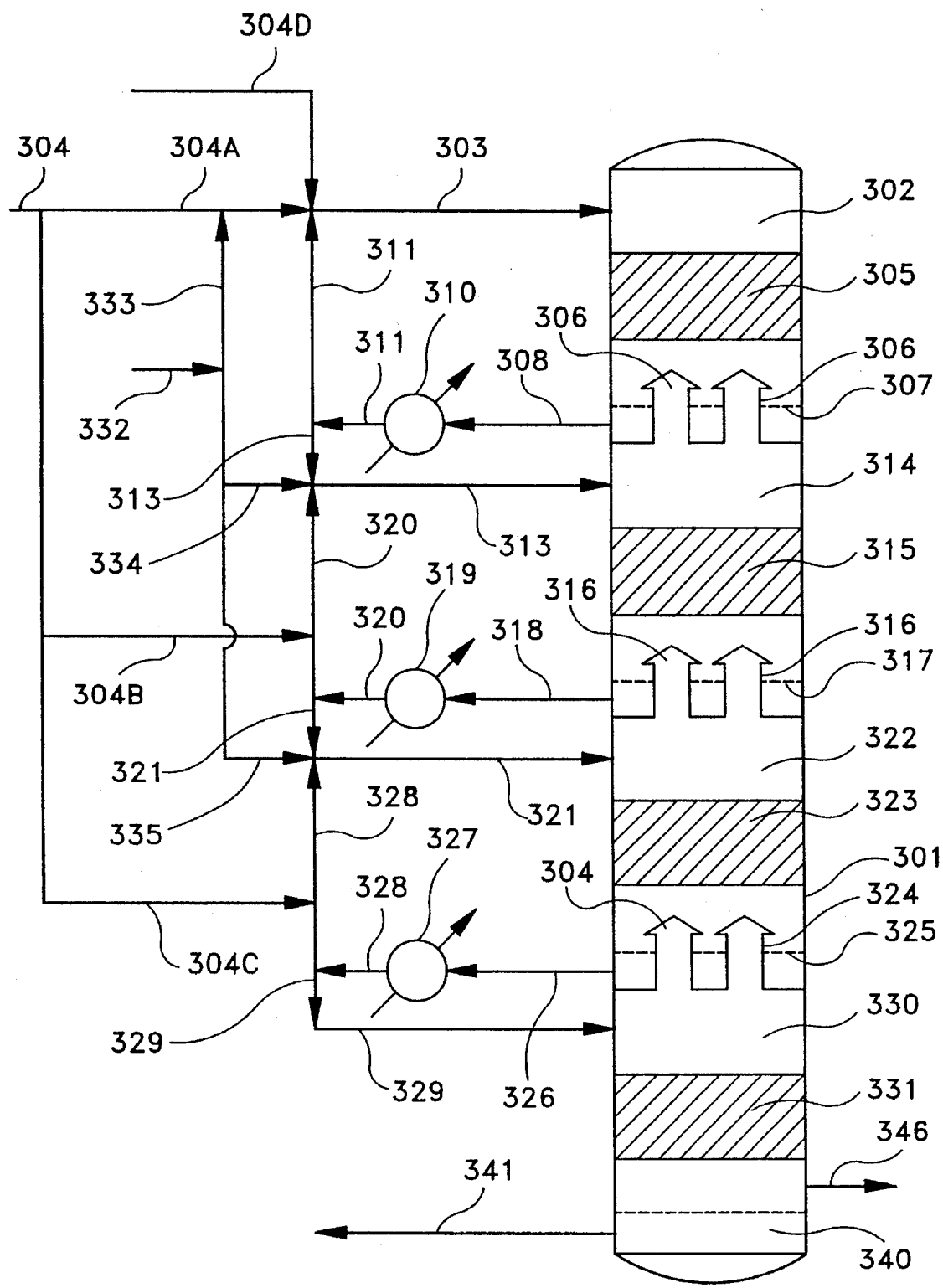

FIG. 3 illustrates a practice of the invention which is analogous to that shown in FIG. 1 except that alcohol diluent is added to the first reaction zone.

With reference to FIG. 2, the system described therein is essentially similar to that of FIG. 1 except that instead of all of the net hydrogen peroxide feed passing via lines 4 and 3 to zone 2, the net hydrogen peroxide feed is split and fed in equal amounts to zones 202, 214 and 222 via lines 204A, 204B and 204C respectively.

With reference to FIG. 3, the system described therein is essentially similar to that of FIG. 2 except that a diluent alcohol stream is added to zone 302 via lines 304D and 303.

The following examples illustrates the invention. In these examples, propylene oxide is produced by the liquid phase reaction of propylene and hydrogen peroxide in accordance with the following reaction:

Solid titanium silicalite is employed as catalyst; see U.S. Pat. No. 5,214,168.

EXAMPLE 1

Referring to FIG. 1, net feed of hydrogen peroxide in isopropanol/water solvent are introduced via line 4 and line 3 to zone 2 with 14 mols/hr. propylene introduced via lines 32 and 33 in combination with 800 mols/hr of recycled reaction mixture via line 11. The total feed to zone 2 comprises by 9.2 mol % propylene, 7.4 mol % hydrogen peroxide, 3.1 mol % propylene oxide, 48.3 mol % isopropanol, and 32 mol % water. The liquid stream entering zone 2 is at 50° C. Purge propylene vapor is introduced into zone 2 via line 45 at the rate of 1 mol/hr.

The liquid passes through catalyst bed 5 wherein propylene and hydrogen peroxide react in accordance with the above equation. The liquid temperature is increased to 58° C. as a result of the reaction exotherm.

The liquid reaction mixture comprised of 8.8 mol % propylene, 7 mol % hydrogen peroxide, 3.5 mol % propylene oxide, 48.2 mol % isopropanol, and 32.5 mol % water passes at the rate of 914 mols/hr from zone 2 via line 8 and is cooled to 50° C. in exchanger 10.

About 800 mols/hr of the cooled mixture is recycled via lines 11 and 3 to zone 2. About 114 mols/hr of the cooled liquid passes via lines 11 and 13 to the next reaction zone 14 together with 800 mols/hr of cooled recycle reaction liquid via line 20 and 4 mols/hr. liquid propylene via lines 32 and 34. The total liquid feed to zone 14 comprises 8.9 mol % propylene, 3.9 mol % hydrogen peroxide, 6.3 mol % propylene oxide, 46.6 mol % isopropanol, and 34.3 mol % water. Temperature of the liquid introduced to zone 14 is 50° C.

In zone 14, the reaction liquid passes through catalyst bed 15 where further reaction in accordance with the above equation takes place. Liquid temperature increases to 58° C. as a result of the reaction exotherm.

Reaction liquid passes from zone 14 via line 18 to exchanger 19 at the rate of 918 mols/hr. This liquid comprises 8.5 mol % propylene, 3.5 mol % hydrogen peroxide, 6.7 mol % propylene oxide, 46.5 mol % isopropanol, and 34.8 mol % water. The liquid is cooled to 50° C. in exchanger 19.

About 800 mols/hr of the cooled mixture is recycled via lines 20 and 13 to zone 14. About 118 mols/hr of the cooled liquid passes via lines 20 and 21 to the next reaction zone 22 together with 800 mols/hr of cooled recycle reaction liquid via line 28 and 4 mols/hr. liquid propylene via lines 32 and 35. The total liquid to zone 22 comprises 8.7 mol % propylene, 0.4 mol % hydrogen peroxide, 9.4 mol % propylene oxide, 45.1 mol % isopropanol, and 36.4 mol % water. Temperature of the liquid introduced to zone 22 is 50° C.

In zone 22, the reaction liquid passes through catalyst bed 23 where further reaction is accordance with the above equation takes place. Liquid temperature increase to 58° C. as a result of the reaction exotherm.

Reaction liquid passes from zone 22 via line 26 to exchanger 27 at the rate of 922 mols/hr. This liquid comprises 8.2 mol % propylene, 0 mol % hydrogen peroxide, 9.9 mol % propylene oxide, 45 mol % isopropanol, and 36.9 mol % water. The liquid is cooled to 50° C. in exchanger 27.

About 800 mols/hr of the cooled mixture is recycled via lines 28 and 21 to zone 22. About 122 mols/hr. of the cooled liquid passes via lines 28 and 29 to the last reaction zone 30.

In zone 30, the reaction liquid passes through catalyst bed 31 where the remaining small reaction takes place. Liquid temperature increase is small, less than 8° C. as a result of the reaction exotherm and about 122 mols/hr. of liquid product is recovered via line 41.

Purge vapor in amount of 1.2 mols/hr. is removed via line 46 and comprises 84 mol % propylene, 8 mol % water and isopropanol, and 8 mol % oxygen.

The overall yield of propylene oxide based on hydrogen peroxide is 90%. This compares with a yield of about 80% which is achieved using conventional tubular reactors wherein the temperature rise in the catalyst exceeds 15° C.

EXAMPLE 2

Referring to FIG. 2, net feed of hydrogen peroxide in isopropanol/water solvent is introduced at the rate of 100 mols/hr via line 204. The feed composition comprises 33 mol % water, 55 mol % isopropanol and 12 mol % hydrogen peroxide. This net hydrogen peroxide feed is divided with 34 mols/hr passing via lines 204A and 203 to zone 202, 33 mols/hr passing via lines 204B, 220 and 213 to zone 214, and 33 mols/hr passing via lines 204C, 228 and 221 to zone 222.

The 34 mols/hr of hydrogen peroxide feed is combined with feed propylene introduced via line 232 and with recycle reaction mixture via line 211 to form a feed mixture to zone 202 via line 203 of 861 mols/hr comprised of 241 mols/hr water, 331 mols/hr isopropanol, 18 mols/hr hydrogen peroxide, 228 mols/hr propylene and 41 mols/hr propylene oxide. This mixture is fed to zone 202 at 54.4° C. and 240 psia.

The liquid passes through catalyst bed 205 wherein propylene and hydrogen peroxide react in accordance with the above equation. The liquid temperature is increased to 60° C. as a result of the reaction exotherm.

The liquid reaction mixture comprised of 25.1 mol % propylene, 1.68 mol % hydrogen peroxide, 5.17 mol % propylene oxide, 38.9 mol % isopropanol, and 28.7 mol % water passes at the rate of 849 mols/hr from zone 202 via line 208 and is cooled to 54.4° C. in exchanger 10.

About 800 mols/hr of the cooled mixture is recycled via lines 211 and 203 to zone 202. About 49 mols/hr of the cooled liquid passes via lines 211 and 213 to the next reaction zone 214 together with 800 mols/hr of cooled recycle reaction liquid via line 220, 25 mols/hr liquid propylene via lines 232 and 234, and 33 mols/hr of the hydrogen peroxide feed. The total liquid feed to zone 214 comprises 26.1 mol % propylene, 1.82 mol % hydrogen peroxide, 5.5 mol % propylene oxide, 37.8 mol % isopropanol, and 28.3 mol % water. Temperature of the liquid introduced to zone 14 is 54.4° C.

In zone 214, the reaction liquid passes through catalyst bed 215 where further reaction in accordance with the above equation takes place. Liquid temperature increases to 60° C. as a result of the reaction exotherm.

Reaction liquid passes from zone 214 via line 218 to exchanger 219 at the rate of 896 mols/hr. This liquid comprises 24.9 mol % propylene, 1.45 mol % hydrogen peroxide, 5.9 mol % propylene oxide, 38.3 mol % isopropanol, and 29.1 mol % water. The liquid is cooled to 54.4° C. in exchanger 219.

About 800 mols/hr of the cooled mixture is recycled via lines 220 and 213 to zone 214. About 96 mols/hr of the cooled liquid passes via lines 220 and 221 to the next reaction zone 222 together with 800 mols/hr of cooled recycle reaction liquid via line 228, 25 mols/hr liquid propylene via lines 232 and 235, and 33 mols/hr of the hydrogen peroxide feed. The total liquid to zone 222 comprises 26.0 mol % propylene, 1.65 mol % hydrogen peroxide, 6.0 mol % propylene oxide, 37.5 mol % isopropanol, and 28.5 mol % water. Temperature of the liquid introduced to zone 222 is 54.4° C.

In zone 222, the reaction liquid passes through catalyst bed 223 where further reaction is accordance with the above equation takes place. Liquid temperature increases to 60° C. as a result of the reaction exotherm.

Reaction liquid passes from zone 222 via line 226 to exchanger 227 at the rate of 943.7 mols/hr. This liquid comprises 24.9 mol % propylene, 1.28 mol % hydrogen peroxide, 6.4 mol % propylene oxide, 37.9 mol % isopropanol, and 29.1 mol % water. The liquid is cooled to 54.4° C. in exchanger 227.

About 800 mols/hr of the cooled mixture is recycled via lines 228 and 221 to zone 222. About 143.7 mols/hr. of the cooled liquid passes via lines 228 and 219 to the last reaction zone 330.

In zone 230, the reaction liquid passes through catalyst bed 231 where the remaining small reaction takes place. Liquid temperature increase is small, less than 8° C. as a result of the reaction exotherm and about 128 mols/hr of liquid product is recovered via line 241.

Purge vapor in amount of 48 mols/hr is removed via line 246 and comprises 92.6 mol % propylene, 0.6 mol % oxygen, 3.8 mol % water and isopropanol, and 3 mol % propylene oxide; this stream is further treated for propylene and propylene oxide recovery (not shown).

The overall yield of propylene oxide based on hydrogen peroxide is 90.8%. This compares with a yield of about 80% which is achieved using conventional tubular reactors wherein the temperature rise in the catalyst exceeds 15° C. The yield is also higher than that is Example 1 due to the separate introduction of hydrogen peroxide feed into the separate zones.

EXAMPLE 3

Referring to FIG. 3, the net hydrogen peroxide composition and feed rate is the same as for Example 2. The net hydrogen peroxide feed passes at the rate of 34 mols/hr via lines 304A and 303 to zone 302, at the rate of 33 mols/hr via lines 304B and 313 to zone 314, and at the rate of 33 mols/hr via lines 304C, 328 and 321 to zone 322. Isopropanol diluent is fed via lines 304D and 303 to zone 302 at the rate of 100 mols/hr.

The 34 mols/hr of hydrogen peroxide feed and 100 mols/hr of isopropanol are combined with feed propylene introduced via line 332 and with recycle reaction mixture via line 311 to form a feed mixture to zone 302 via line 303 of 806 mols/hr comprised of 54.1 mols/hr water, 464.5 mols/hr isopropanol, 7.1 mols/hr hydrogen peroxide, 271.2 mols/hr propylene and 8.2 mols/hr propylene oxide. This mixture is fed to zone 302 at 54.4° C. and 240 psia.

The liquid passes through catalyst bed 305 wherein propylene and hydrogen peroxide react in accordance with the above equation. The liquid temperature is increased to 60° C. as a result of the reaction exotherm.

The liquid reaction mixture comprised of 33.3 mol % propylene, 0.5 mol % hydrogen peroxide, 1.35 mol % propylene oxide, 57.6 mol % isopropanol, and 7.1 mol % water passes at the rate of 806 mols/hr from zone 302 via line 308 and is cooled to 54.4° C. in exchanger 310.

About 600 mols/hr of the cooled mixture is recycled via lines 311 and 303 to zone 302. About 206 mols/hr of the cooled liquid passes via lines 211 and 213 to the next reaction zone 214 together with 600 mols/hr of cooled recycle reaction liquid via line 220 and 25 mols/hr liquid propylene via lines 332 and 334, and 33 mols/hr of the hydrogen peroxide feed via line 304B. The total liquid feed to zone 314 comprises 34.2 mol % propylene, 1.03 mol % hydrogen peroxide, 1.9 mol % propylene oxide, 52.2 mol % isopropanol, and 10.5 mol % water. Temperature of the liquid introduced to zone 14 is 54.4° C.

In zone 314, the reaction liquid passes through catalyst bed 315 where further reaction in accordance with the above equation takes place. Liquid temperature increases to 60° C. as a result of the reaction exotherm.

Reaction liquid passes from zone 314 via line 318 to exchanger 319 at the rate of 860.9 mols/hr. This liquid comprises 33.6 mol % propylene, 0.65 mol % hydrogen peroxide, 2.24 mol % propylene oxide, 52.4 mol % isopropanol, and 10.9 mol % water. The liquid is cooled to 54.4° C. in exchanger 319.

About 600 mols/hr of the cooled mixture is recycled via lines 320 and 313 to zone 314. About 260.9 mols/hr of the cooled liquid passes via lines 320 and 321 to the next reaction zone 322 together with 600 mols/hr of cooled recycle reaction liquid via line 328, 25 mols/hr liquid propylene via lines 332 and 335, and 33 mols/hr of the hydrogen peroxide feed via line 304C. The total liquid to zone 322 comprises 33.2 mol % propylene, 1.04 mol % hydrogen peroxide, 2.54 mol % propylene oxide, 49.76 mol % isopropanol, and 13.32 mol % water. Temperature of the liquid introduced to zone 22 is 54.4° C.

In zone 322, the reaction liquid passes through catalyst bed 323 where further reaction is accordance with the above equation takes place. Liquid temperature increases to 60° C. as a result of the reaction exotherm.

Reaction liquid passes from zone 322 via line 326 to exchanger 327 at the rate of 908.2 mols/hr. This liquid comprises 32.1 mol % propylene, 0.68 mol % hydrogen peroxide, 2.9 mol % propylene oxide, 50.32 mol % isopropanol, and 13.84 mol % water. The liquid is cooled to 54.4° C. in exchanger 327.

About 600 mols/hr of the cooled mixture is recycled via lines 328 and 321 to zone 322. About 308 mols/hr. of the cooled liquid passes via lines 328 and 329 to the last reaction zone 330.

In zone 330, the reaction liquid passes through catalyst bed 331 where the remaining small reaction takes place. Liquid temperature increase is small, less than 8° C. as a result of the reaction exotherm and about 315 mols/hr. of liquid product is recovered via line 341.

Purge vapor in amount of 5 mols/hr. is removed via line 346 and comprises 92 mol % propylene, 4 mol % water and isopropanol, and 4 mol % oxygen.

The overall yield of propylene oxide based on hydrogen peroxide is 92%. This compares with a yield of about 80% which is achieved using conventional tubular reactors wherein the temperature rise in the catalyst exceeds 15° C. The yield is higher than that for Example 2 due to the lower concentrations of propylene oxide and hydrogen peroxide in the reaction zones.

I claim:

1. A continuous process for the exothermic reaction of propylene and hydrogen peroxide in the liquid phase to produce propylene oxide in a series of separate reaction zones each containing a packed bed of solid catalyst, wherein a reaction liquid comprised of propylene, hydrogen peroxide and propylene oxide as well as a vapor purge stream is passed through the bed of the solid catalyst at reaction conditions in each of the reaction zones, the resulting mixture is separated in each zone into a vapor stream which passes to the next reaction zone and a reaction liquid stream, the reaction liquid stream from each zone is removed and separately cooled to remove exothermic heat of reaction generated in the zone from which the liquid was removed, 60–90% of the cooled liquid is recycled to the zone from which it was removed and 10–40% of the cooled liquid is passes to the next in the series of reaction zones.

2. The process of claim 1 wherein a propylene vapor stream is passed through the series of reaction zones to purge oxygen generated therein.

3. The process of claim 1 wherein a portion of the net hydrogen peroxide feed is fed to each reaction zone.

4. The process of claim 1 wherein a diluent liquid is fed to the first of the series of reaction zones.

5. The process of claim 4 wherein the diluent liquid is isopropanol.

6. The process of claim 4 wherein the diluent liquid is a mixture of isopropanol and methanol.

* * * * *